US008043331B2

(12) United States Patent
Pugsley et al.

(10) Patent No.: US 8,043,331 B2
(45) Date of Patent: Oct. 25, 2011

(54) IMPERMANENT BIOCOMPATIBLE FASTENER

(75) Inventors: Charles H. Pugsley, Pelham, NH (US); Joseph A. Levendusky, Groton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 428 days.

(21) Appl. No.: 12/285,468

(22) Filed: Oct. 6, 2008

(65) Prior Publication Data

US 2009/0118748 A1    May 7, 2009

Related U.S. Application Data

(63) Continuation of application No. 10/712,966, filed on Nov. 12, 2003, now Pat. No. 7,442,201, which is a continuation of application No. 09/935,950, filed on Aug. 23, 2001, now Pat. No. 6,692,507.

(51) Int. Cl.
*A61B 17/08*    (2006.01)
*A61B 17/56*    (2006.01)

(52) U.S. Cl. .............................. 606/220; 606/76; 606/219

(58) Field of Classification Search .................. 606/300, 606/301, 75–77, 151, 153, 154, 219, 220
See application file for complete search history.

(56) References Cited

U.S. PATENT DOCUMENTS

| | | | |
|---|---|---|---|
| 3,974,835 A | 8/1976 | Hardy, Jr. |
| 4,060,089 A | 11/1977 | Noiles |
| 4,338,926 A | 7/1982 | Kummer et al. |
| 4,402,445 A | 9/1983 | Green |
| 4,724,839 A | 2/1988 | Bedi et al. |
| 4,889,119 A | 12/1989 | Jamiolkowski et al. |
| 4,932,960 A | 6/1990 | Green et al. |
| 5,080,665 A | 1/1992 | Jarrett et al. |
| 5,169,400 A | 12/1992 | Mühling et al. |
| 5,258,012 A | 11/1993 | Luscombe et al. |
| 5,346,501 A | 9/1994 | Regula et al. |
| 5,522,817 A | 6/1996 | Sander et al. |
| 5,725,529 A | 3/1998 | Nicholson et al. |
| 5,968,044 A | 10/1999 | Nicholson et al. |
| 5,984,927 A | 11/1999 | Wenstrom, Jr. et al. |
| 6,022,352 A | 2/2000 | Vandewalle |

(Continued)

FOREIGN PATENT DOCUMENTS

AU    20023337000    5/2005

(Continued)

OTHER PUBLICATIONS

International Search report dated Dec. 12, 2002, from corresponding PCT Appln. No. PCT/EP02/09466.

(Continued)

*Primary Examiner* — Julian Woo
(74) *Attorney, Agent, or Firm* — Finnegan, Henderson, Farabow, Garrett & Dunner LLP

(57) ABSTRACT

An embodiment of the invention includes a method of fastening together two tissue portions. The method may include positioning a medical device adjacent a region of tissue having two tissue portions. The medical device may include a male member and a female member having a first bioabsorbable material overlying one of a non-bioabsorbable material and a second bioabsorbable material. The first bioabsorbable material may have a first degradation rate, and the second bioabsorbable material may have a second degradation rate slower than the first degradation rate. The method may also include inserting the male member inside the female member so as to inhibit withdrawal of the male member from the female member with the two tissue portions between the male member and the female member.

26 Claims, 7 Drawing Sheets

U.S. PATENT DOCUMENTS

| | | |
|---|---|---|
| 6,044,847 A | 4/2000 | Carter et al. |
| 6,086,600 A | 7/2000 | Kortenbach |
| 6,113,609 A | 9/2000 | Adams |
| 6,258,121 B1 | 7/2001 | Yang et al. |
| 6,290,701 B1 | 9/2001 | Enayati |
| 6,471,707 B1 | 10/2002 | Miller et al. |
| 6,503,259 B2 | 1/2003 | Huzel et al. |
| 6,620,194 B2 | 9/2003 | Ding et al. |
| 6,692,507 B2 | 2/2004 | Pugsley et al. |
| 2002/0088252 A1 | 7/2002 | Zhang et al. |
| 2004/0097987 A1 | 5/2004 | Pugsley et al. |

FOREIGN PATENT DOCUMENTS

| | | |
|---|---|---|
| CA | 2426639 | 3/2007 |
| EP | 0390613 | 10/1990 |
| EP | 1418848 | 2/2007 |
| WO | WO-00/40159 | 7/2000 |
| WO | WO-00/57796 | 10/2000 |

OTHER PUBLICATIONS

Middleton et al., 'Synthetic Biodegradable Polymers as Medical Devices,' Medical Plastics and Biomaterials (Mar. 1998).

IMPERMANENT BIOCOMPATIBLE FASTENER

This is a continuation application of U.S. patent application Ser. No. 10/712,966, filed Nov. 12, 2003 now U.S. Pat. No. 7,442,201, which is a continuation application of U.S. patent application Ser. No. 09/935,950, filed Aug. 23, 2001 now U.S. Pat. No. 6,692,507, the entirety of which are incorporated herein by reference.

BACKGROUND OF THE INVENTION

The present invention relates generally to biocompatible fasteners and more particularly to impermanent biocompatible fasteners.

Biocompatible fasteners have long been used to fasten together two or more biological materials on or within a patient. Examples of biocompatible fasteners include sutures, staples, surgical glues, tissue clips and orthopedic fixation devices, such as bone plates, screws and the like. For certain applications, such as where the biocompatible fastener is implanted within a patient and is needed therewithin for only a limited period of time, it is highly desirable that the biocompatible fastener be impermanent or capable of degrading over time so that an additional medical procedure not be required to remove the fastener from the patient. For this reason, many biocompatible fasteners now in use are made entirely out of materials that, over time, become chemically degraded within a patient and, ultimately, are fully metabolized and excreted by the patient. (Other biocompatible fasteners are made out of materials that the body needs and are not excreted.) Such impermanent biocompatible fasteners are typically referred to in the art as bioabsorbable fasteners and are made out of materials including, but not limited to, homopolymers and copolymers of glycolide, lactide, $\epsilon$-caprolactone and p-dioxanone, copolymers of glycolide and trimethylene carbonate, as well as polyanhydrides and polyorthoesters. See Middleton et al., "Synthetic Biodegradable Polymers as Medical Devices," *Medical Plastics and Biomaterials* (March 1998), the disclosure of which is incorporated herein by reference.

Gastroesphageal reflux disease (GERD) is a disorder in which the lower esophageal sphincter, which is located in a distal portion of the esophagus adjacent to the junction between the esophagus and the stomach, allows contents of the stomach, including gastric acid and bile, to reverse flow into the distal portion of the esophagus during digestion. Complications associated with GERD include heartburn, pulmonary disorders, chest pain, esophageal ulcers, esophagitis, Barrett's esophagus, and esophageal carcinoma.

Although weight loss and/or prescription acid blockers are typically preferred treatment options for GERD, various surgical procedures have been devised to treat GERD where weight loss and/or prescription drugs are ineffective or impractical. In one surgical procedure, known as Nissen fundoplication, a portion of the gastric fundus of the stomach is wrapped around the esophagus and is secured thereto using one or more biocompatible fasteners, typically in the form of sutures, surgical staples or surgical two-part fasteners. The wrapped gastric fundus applies pressure to the esophagus in such a way as to eliminate the reverse flow of stomach contents into the esophagus.

One of the more commonly used fundoplication procedures requires abdominal or thoracic incisions through which the fundus wrapping and securing can be performed. Due to the highly invasive nature of such surgery, complications and morbidity occur in a significant percentage of cases. In addition, these procedures are time-consuming, often taking a number of hours to perform, and may leave disfiguring scars where the incisions were made.

More recently developed fundoplication procedures limit somewhat the necessity of making large surgical incisions by utilizing laproscopic ports or percutaneous endoscopic gastrostomy. Although these procedures are less invasive than those involving large abdominal and thoracic incisions, they are still invasive and have certain risks associated therewith. For example, general anaesthesia, which entails well-known risks, is typically used during these procedures.

An even more recently developed fundoplication procedure is endoluminal fundoplication. In endoluminal fundoplication, a flexible endoscope is passed first through a patient's mouth and then through the esophagus to locate an attachment site at the gastroesophageal junction. A tissue grasping device is then positioned at the distal end of the endoscope and is attached to the located attachment site. Next, a tissue displacement device is positioned at the distal end of the endoscope and is used to displace the fundus of the stomach in such a way as to create an intussusception of the esophagus into the gastric lumen. A fastener delivery device is then used to secure the gastric fundus to the esophagus at a first location. The fastener delivery device is then used to place additional fasteners at a plurality of additional desired fastener locations, thus securing the gastric fundus entirely around the esophagus.

Examples of endoluminal fundoplication procedures are disclosed in U.S. Pat. No. 6,086,600, inventor Kortenbach, which issued Jul. 11, 2000, and in U.S. Pat. No. 6,113,609, inventor Adams, which issued Sep. 5, 2000, both of which are incorporated herein by reference.

In the aforementioned U.S. Pat. No. 6,113,609, there is disclosed a fundoplication fastener that is made entirely out of a bioabsorbable material. One problem that has been noted by the present inventors is that, whereas a fundoplication fastener need only be capable of securing the gastric fundus to the esophagus for the approximately three- to six-month period of time necessary for the gastric fundus and the esophagus to become fused to one another, a bioabsorbable fundoplication fastener typically will remain in place for approximately two years before chemical degradation results in its structural decay.

SUMMARY OF THE INVENTION

It is an object of the present invention to provide a novel biocompatible fastener.

Therefore, according to one aspect of the invention, there is provided a biocompatible fastener, said biocompatible fastener having a first portion and a second portion, said first portion being made out of a first bioabsorbable material, said first bioabsorbable material having a first degradation rate, said second portion being made out of a material selected from the group consisting of a non-bioabsorbable material and a second bioabsorbable material, said second bioabsorbable material having a second degradation rate, said second degradation rate being slower than said first degradation rate.

It is another object of the present invention to provide a novel impermanent biocompatible fastener.

Therefore, according to another aspect of the invention, there is provided a biocompatible fastener as described above wherein said first portion is positioned within said biocompatible fastener so that degradation of said first portion results in fragmentation of the biocompatible fastener.

It is still another object of the present invention to provide an impermanent biocompatible fastener that overcomes at least some of the shortcomings discussed above in connection with existing impermanent biocompatible fasteners.

Therefore, according to still another aspect of the invention, there is provided a biocompatible fastener that comprises, in a preferred embodiment, a male portion and a female portion. The male portion includes a first base member, the first base member being generally flat and oval. A pair of male members are mounted on the bottom surface of the first base member, each male member comprising a cylindrical post extending downwardly from the bottom surface of the first base member and a conical head disposed at the bottom end of the post. The female portion includes a second base member, the second base member being generally flat and oval. A pair of sleeves are mounted on the top surface of the second base member and extend upwardly therefrom. Each sleeve defines a bore adapted to receive a head from a corresponding male member and is provided with a pair of longitudinal slots that endow the sleeve with some radial flexibility to facilitate insertion of a head into the bore. In addition, each sleeve is provided with a sharp tip at its top end to facilitate insertion of the sleeve through biological tissue. A substantially circumferential flange is formed on the inside of each sleeve. The flange extends radially into the bore and is engageable with the head once the head has been inserted therepast so as to inhibit premature withdrawal of the head from the bore. Except for an outer coating on each of the two heads, the fastener is made entirely of a non-bioabsorbable material. By contrast, the outer coating of the heads is made of a bioabsorbable material having a desired degradation rate. The thickness of the outer coating is appropriately selected so that degradation of the outer coating after a desired period of time permits each head to be withdrawn past its flange.

Because the heads of the aforementioned fastener are not made entirely of a bioabsorbable material, but rather, are made of an inner core of a non-bioabsorbable material and an outer coating of a bioabsorbable material, the thickness of the bioabsorbable material is less than it would otherwise be in a corresponding head made entirely out of the bioabsorbable material. Consequently, because of its reduced thickness, the bioabsorbable material becomes fully hydrated more rapidly and, therefore, degrades more quickly in the present fastener than in a corresponding fastener made entirely out of bioabsorbable material. As a result, by selecting an appropriate bioabsorbable material and by dimensioning the fastener appropriately, the life-span of the fastener can be tailored to the healing time for the fastened biological material, e.g., three to six months for tissue subjected to a fundoplication procedure.

As can readily be appreciated, instead of or in addition to making the heads out of an inner core of non-bioabsorbable material and an outer coating of bioabsorbable material, the flanges can be made out of an inner core of non-bioabsorbable material and an outer coating of bioabsorbable material. A variety of other modifications to the aforementioned fasteners are also possible.

The above-described fasteners are amenable to being mass-produced by conventional molding techniques.

For purposes of the present specification and claims, it is to be understood that certain directional terms used herein, such as "top," "bottom," "upwardly," "downwardly," and the like, when used to describe the fastener of the present invention, are relative terms dependent upon the fastener being situated in a particular orientation vis-à-vis the viewer at a particular-point in time. As can readily be appreciated, if the orientation of the fastener is altered, such directional terms may also need to be altered correspondingly.

Additional objects, features, aspects and advantages of the present invention will be set forth, in part, in the description which follows and, in part, will be obvious from the description or may be learned by practice of the invention. In the description, reference is made to the accompanying drawings which form a part thereof and in which is shown by way of illustration specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate preferred embodiments of the invention and, together with the description, serve to explain the principles of the invention. In the drawings wherein like reference numerals represent like parts.

DETAILED DESCRIPTION OF PREFERRED EMBODIMENTS

Figure 2:
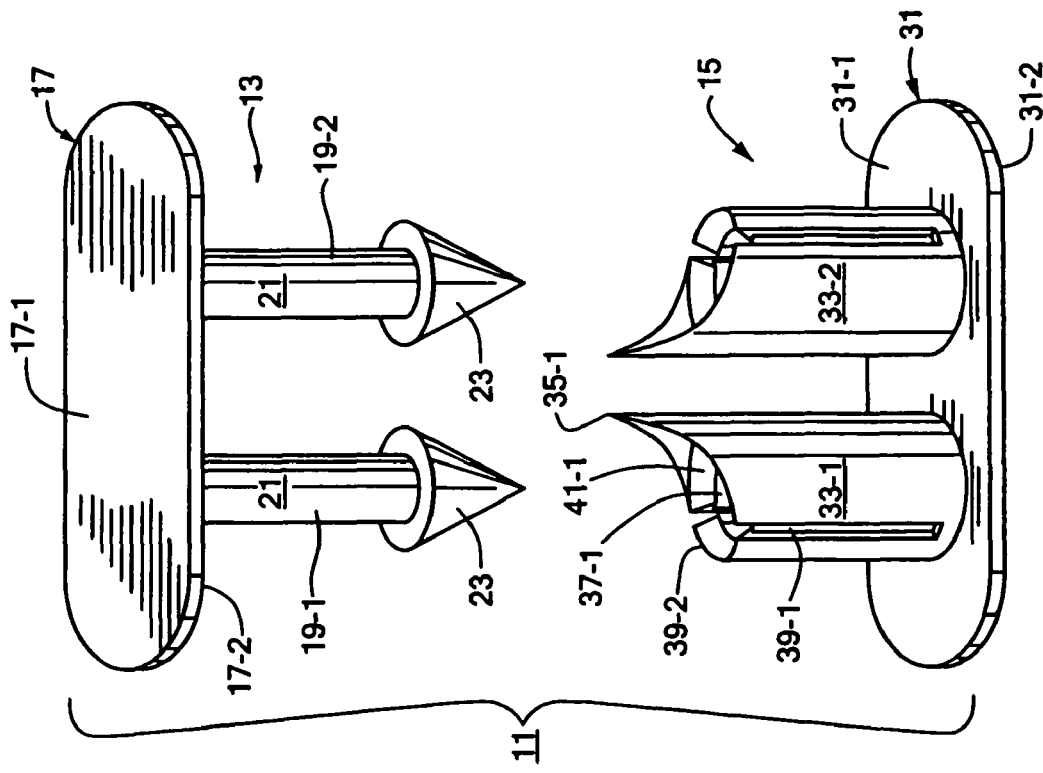
FIG. 2 is a perspective view of the biocompatible fastener of FIG. 1, the biocompatible fastener being shown in an unassembled state.
Figure 1:
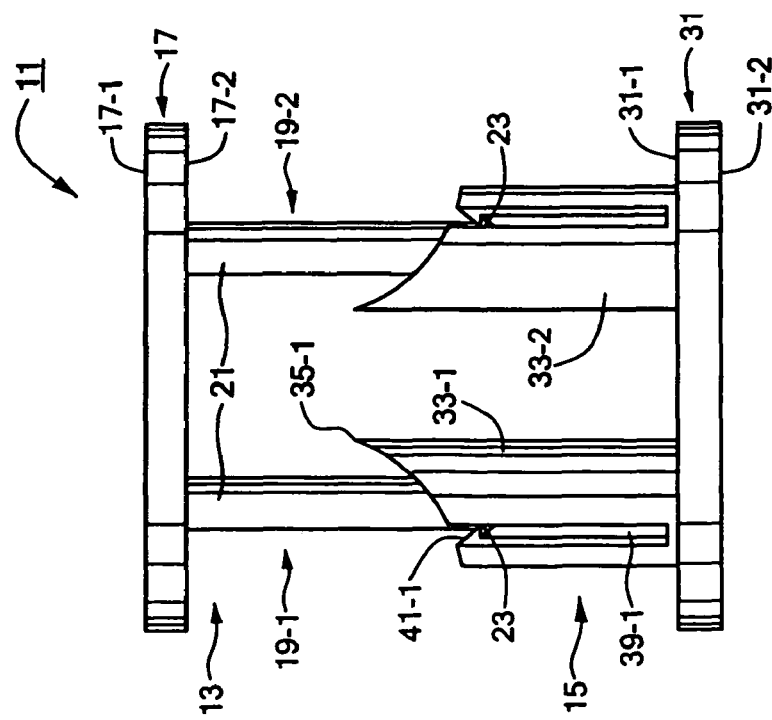
FIG. 1 is a front view of a first embodiment of a biocompatible fastener constructed according to the teachings of the present invention, the biocompatible fastener being shown in an assembled state.
Figure 3:
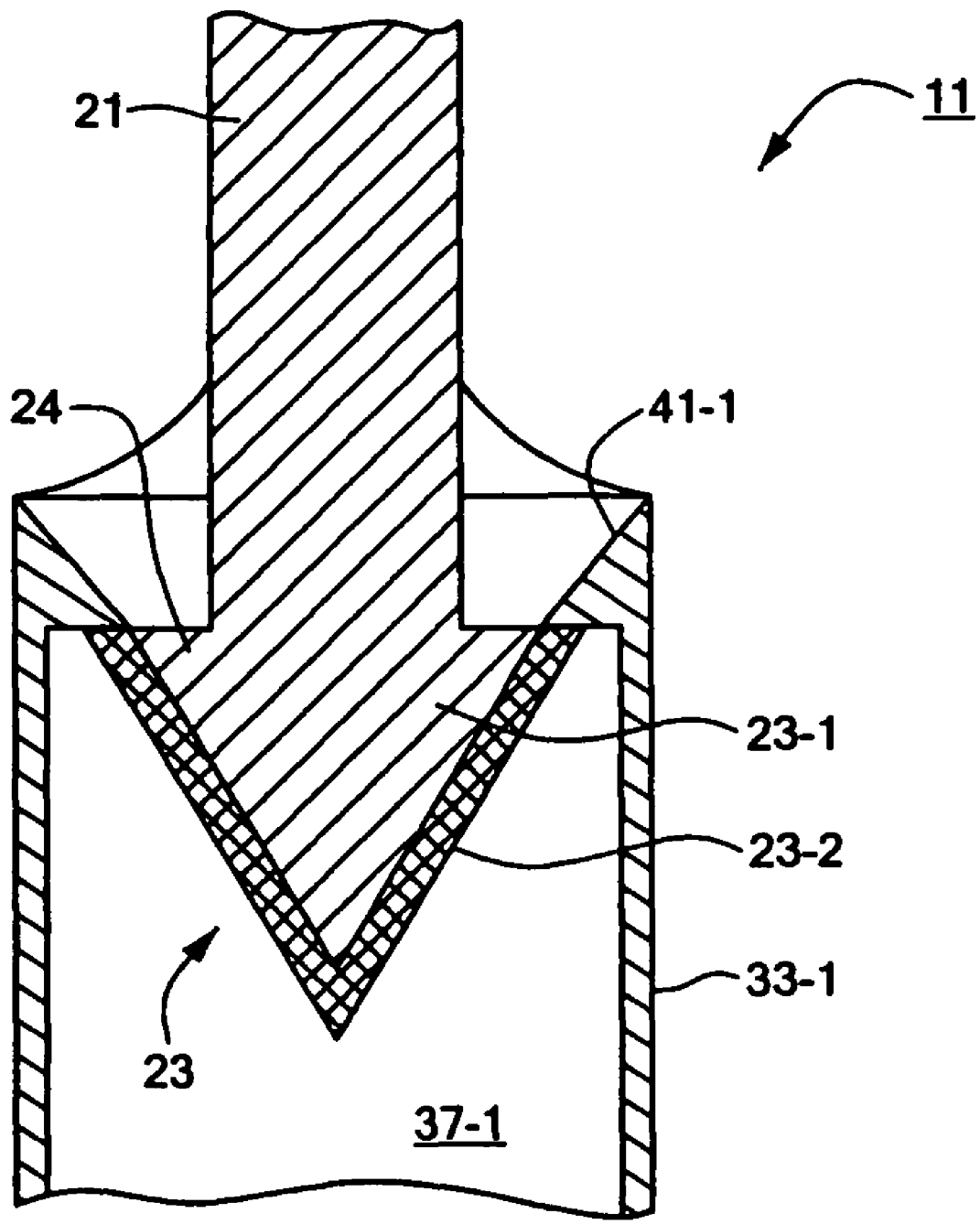
FIG. 3 is a fragmentary section view of the biocompatible fastener of FIG. 1.

Referring now to FIGS. 1 through 3, there are shown various views of a first embodiment of a biocompatible fastener constructed according to the teachings of the present invention, said biocompatible fastener being represented generally by reference numeral 11.

Fastener 11, which is particularly well-suited for, but is not limited to, temporarily securing the gastric fundus to the esophagus as part of a fundoplication procedure, is a two-piece, mating-type fastener comprising a male portion 13 and a female portion 15.

Male portion 13, which may be made by molding, is a generally rigid structure comprising a base 17. Base 17, which is generally flat and oval, has a top surface 17-1 and a bottom surface 17-2. A pair of parallel male members 19-1 and 19-2 are disposed on opposite sides of the transverse centerline of base 17 and extend downwardly a short distance from bottom surface 17-2 of base 17. Male members 19-1 and 19-2 are substantially identical to one another, each male member 19 comprising a generally cylindrical post 21 terminating at its bottom end in a generally conical head 23.

Female portion 15, which may be made by molding, is a generally rigid structure comprising a base 31. Base 31, which is generally flat and oval, has a top surface 31-1 and a bottom surface 31-2. A pair of generally cylindrical, parallel sleeves 33-1 and 33-2 extend upwardly a short distance from top surface 31-1 of base 31, sleeves 33-1 and 33-2 being spaced apart appropriately for alignment with male members 19-1 and 19-2, respectively. Sleeves 33-1 and 33-2 are substantially mirror images of one another taken along the transverse centerline of base 33, and it is to be understood that the description below of sleeve 33-1 is correspondingly applicable to sleeve 33-2.

Sleeve 33-1 terminates at its top end in a relatively sharp tip 35-1, tip 35-1 being so shaped to facilitate insertion of sleeve 33-1 through biological tissue or the like. Sleeve 33-1 is additionally shaped to include a longitudinally-extending bore 37-1 adapted to receive male member 19-1. A pair of longitudinally-extending slots 39-1 and 39-2 that are in fluid communication with bore 37-1 are provided in sleeve 33-1 to endow sleeve 33-1 with a certain degree of radial flexibility to facilitate insertion of member 19-1 into bore 37-1. However, it should be understood that, depending upon the applicable flexibility requirements of sleeve 33-1, one or both of slots 39-1 and 39-2 could be changed in size or eliminated entirely and that one or more additional slots could be provided in sleeve 33-1.

Sleeve 33-1 is further shaped to include a substantially circumferential flange 41-1, flange 41-1 extending radially inwardly a short distance into bore 37-1. Flange 41-1 is appropriately sized so that, once head 23 is inserted into bore 37-1 and past flange 41-1, head 23 cannot easily be withdrawn from bore 37-1 back past flange 41-1, except under the conditions described below.

Referring now to FIG. 3, head 23 can be seen to comprise a core 23-1 and a coating 23-2. Core 23-1 is made out of a non-bioabsorbable material, and coating 23-2 is made out of a bioabsorbable material having a desired degradation rate. Said non-bioabsorbable material used to make core 23-1 may be conventional in nature and may comprise one or more non-bioabsorbable compounds. Said bioabsorbable material used to make coating 23-2 may also be conventional in nature and may comprise one or more bioabsorbable compounds.

The remainder of male portion 13 (and the entirety of female portion 15) is preferably made entirely out of the same non-bioabsorbable material as core 23-1. Head 23 may be formed by insert molding coating 23-2 onto core 23-1. Core 23-1 and coating 23-2 are appropriately sized relative to flange 41-1 so that, when coating 23-2 becomes sufficiently degraded after having been implanted within a patient for a particular period of time, head 23 shrinks in size until head 23 is no longer retained in bore 37-1 by flange 41-1. (In other words, top surface 24 of head 23 is no longer engaged by flange 41-1.)

As can readily be appreciated, fastener 11 has a shorter life-span (i.e., will fragment sooner) than a corresponding fastener made entirely out of a bioabsorbable material for the reason that the thickness of the bioabsorbable material in fastener 11 is considerably less than that in a corresponding "all-bioabsorbable" fastener. Consequently, because of its reduced thickness, the bioabsorbable material of fastener 11 takes less time to become fully hydrated and, therefore, degrades more rapidly than a corresponding "all-bioabsorbable" fastener.

It should be understood that one can alter the life-span of fastener 11 by, among other things, modifying the type of bioabsorbable material used in coating 23-2, modifying the thickness of coating 23-2, and modifying the relative dimensions of core 23-1, coating 23-2 and flange 41-1. It should also be understood that the non-bioabsorbable material used to make all of fastener 11, except for coating 23-2, could be replaced with one or more bioabsorbable materials having a slower degradation rate than the bioabsorbable material used to make coating 23-2.

In addition, it should be understood that the number of sets of male members 19 and sleeves 33 in fastener 11 is illustrative only and that, in other embodiments, there could be as few as one male member 19 and one sleeve 33 or as many as three or more sets of male members 19 and sleeves 33.

Figure 4:
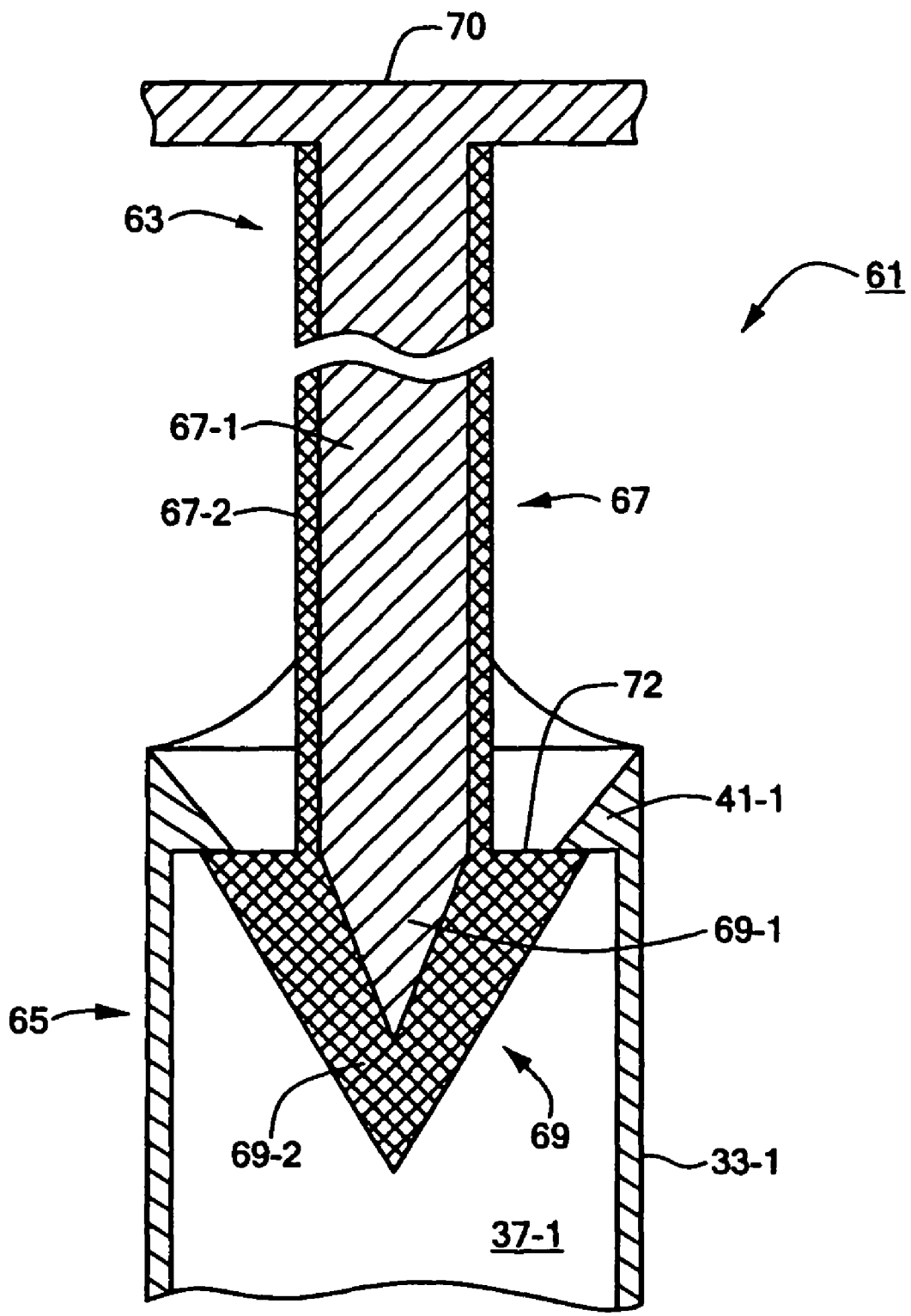
FIG. 4 is a fragmentary section view of a second embodiment of a biocompatible fastener constructed according to the teachings of the present invention, the biocompatible fastener being shown in an assembled state.

Referring now to FIG. 4, there is shown a fragmentary section view of a second embodiment of a biocompatible fastener constructed according to the teachings of the present invention, the biocompatible fastener being shown represented generally by reference numeral 61.

Fastener 61 is similar in many respects to fastener 11, fastener 61 comprising a male portion 63 and a female portion 65, male portion 63 being identical in overall size and shape to male portion 13 of fastener 11, female portion 65 being identical in all respects to female portion 15 of fastener 11.

The principal difference between fastener 61 and fastener 11 is that male portion 63 of fastener 61 is constructed to comprise, instead of a pair of posts 21 each terminating at its bottom end in a generally conical head 23, a pair of posts 67 each terminating at its bottom end in a generally conical head 69 (only one such post 67 and head 69 being shown and described herein although it is to be understood that the two post/head combinations are identical).

Post 67, which is cylindrical in shape, comprises a core 67-1 and a coating 67-2. Core 67-1 is made out of a non-bioabsorbable material, and coating 67-2 is made out of a bioabsorbable material having a desired degradation rate. Said non-bioabsorbable material used to make core 67-1 may be conventional in nature and may comprise one or more non-bioabsorbable compounds. Said bioabsorbable material used to make coating 67-2 may also be conventional in nature and may comprise one or more bioabsorbable compounds.

Head 69, which is conical in shape, comprises a core 69-1 and a coating 69-2. Core 69-1 is made out of a non-bioabsorbable material, and coating 69-2 is made out of a bioabsorbable material having a desired degradation rate. Said non-bioabsorbable material used to make core 69-1 may be conventional in nature and may comprise one or more non-bioabsorbable compounds. Said bioabsorbable material used to make coating 69-2 may also be conventional in nature and may comprise one or more bioabsorbable compounds.

Coating 67-2 is appropriately sized relative to flange 41-1 so that, when coating 67-2 becomes sufficiently degraded after having been implanted within a patient for a particular period of time, head 69 shrinks in size until head 69 is no longer retained in bore 37-1 by flange 41-1. As can be seen, as contrasted with head 23 of fastener 11, the entirety of the top surface 72 of head 69 of fastener 61 is made of bioabsorbable material. This may be advantageous as it may prevent tissue or other matter disposed on top surface 72 from being snagged by top surface 72 and, in so doing, hindering the desired breaking apart of fastener 61.

Cores 67-1 and 69-1 are preferably molded as a unitary structure with base 70, with coatings 67-2 and 69-2 being simultaneously insert molded thereover as a unitary coating.

It should be understood that one can alter the life-span of fastener 61 by, among other things, modifying the type of bioabsorbable material used in coatings 67-2 and 69-2, modifying the thicknesses of coatings 67-2 and 69-2, and modifying the relative dimensions of core 69-1, coating 69-2 and flange 41-1. It should also be understood that the non-bioabsorbable material used to make all of fastener 61, except for coatings 67-2 and 69-2, could be replaced with one or more bioabsorbable materials having a slower degradation rate than the bioabsorbable material used to make coatings 67-2 and 69-2.

Figure 5:
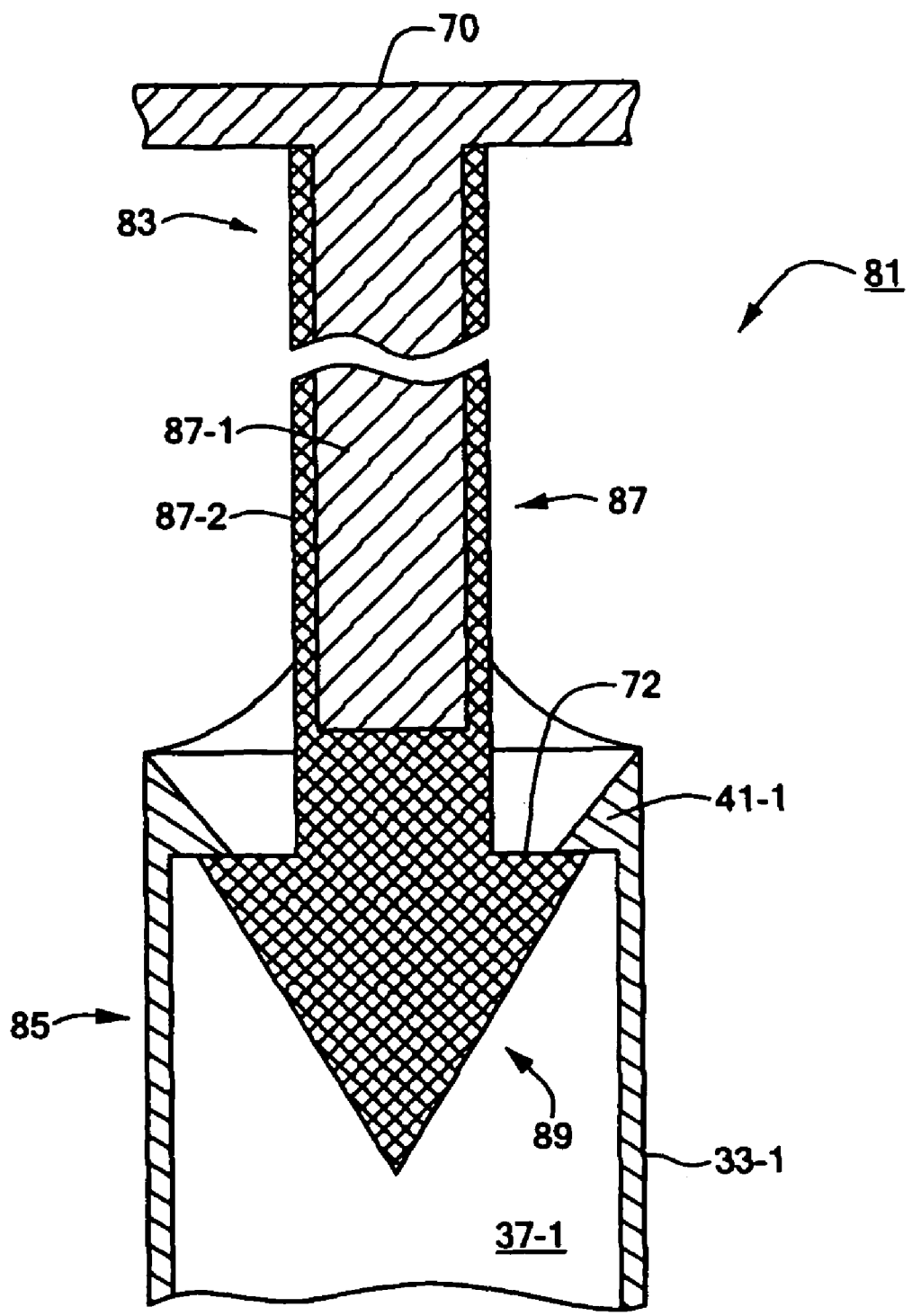
FIG. 5 is a fragmentary section view of a third embodiment of a biocompatible fastener constructed according to the teachings of the present invention, the biocompatible fastener being shown in an assembled state.

Referring now to FIG. 5, there is shown a fragmentary section view of a third embodiment of a biocompatible fastener constructed according to the teachings of the present invention, the biocompatible fastener being shown represented generally by reference numeral 81.

Fastener 81 is similar in many respects to fastener 61, fastener 81 comprising a male portion 83 and a female portion 85, male portion 83 being identical in overall size and shape to male portion 63 of fastener 61, female portion 85 being identical in all respects to female portion 65 of fastener 11.

The principal difference between fastener 81 and fastener 61 is that the bottom portion of post 87 and the entirety of head 89 are made only of bioabsorbable material whereas the remainder of post 87 comprises a core 87-1 made out of a non-bioabsorbable material and a coating 87-2 made out of a bioabsorbable material having a desired degradation rate. As can readily be appreciated, the relative lengths of core 87-1 and post 87 can be modified as desired. It is to be noted that, because head 89 is made entirely out of bioabsorbable material, as opposed to comprising a coating of bioabsorbable material formed on a non-bioabsorbable core, head 89 may take comparatively longer to become fully hydrated.

Figure 7:
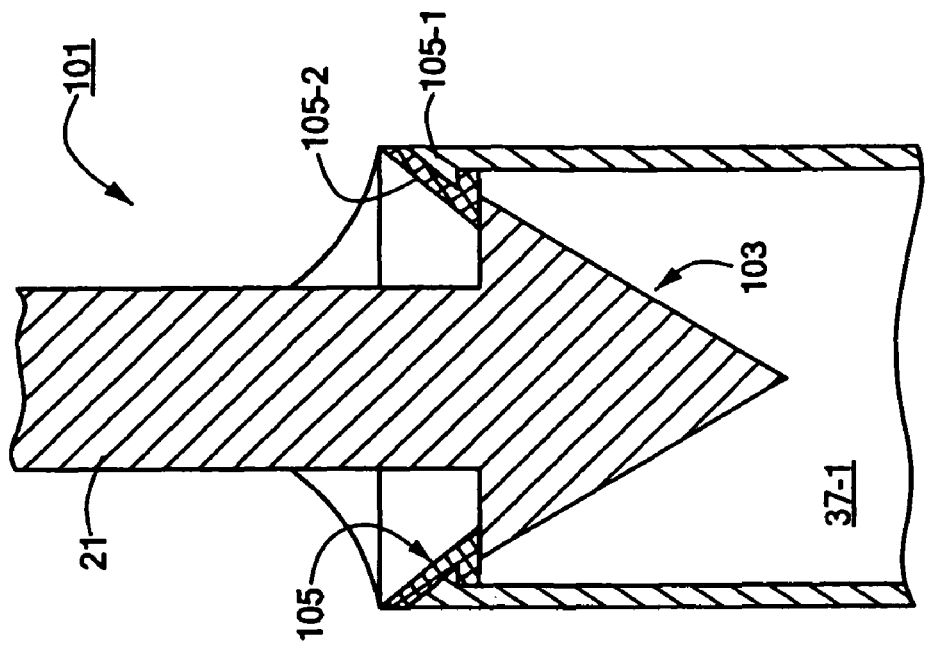
FIG. 7 is a fragmentary section view of the biocompatible fastener of FIG. 6.
Figure 6:
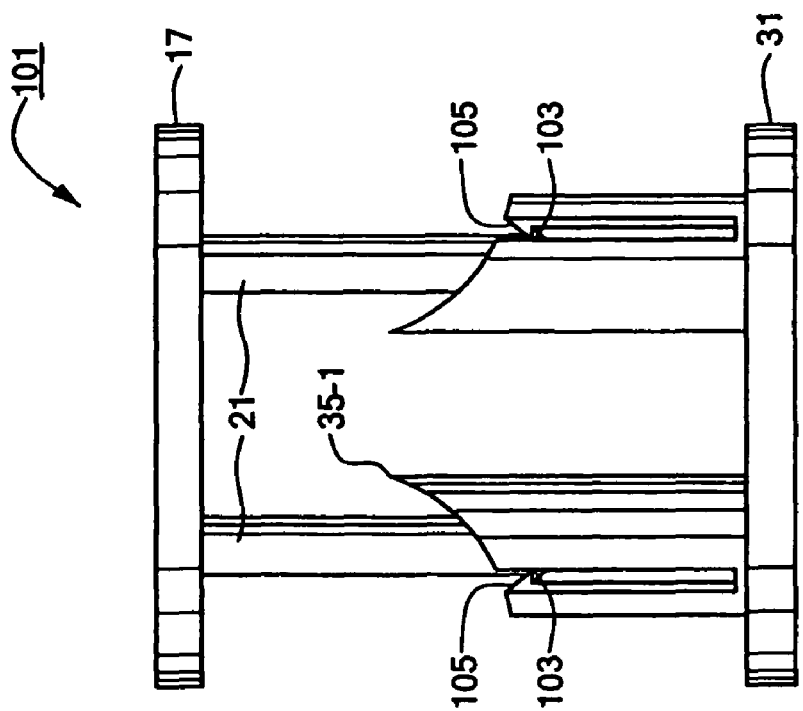
FIG. 6 is a front view of a fourth embodiment of a biocompatible fastener constructed according to the teachings of the present invention, the biocompatible fastener being shown in an assembled state.

Referring now to FIGS. 6 and 7, there are shown front and fragmentary section views, respectively, of a fourth embodiment of a biocompatible fastener constructed according to the teachings of the present invention, said biocompatible fastener being represented generally by reference numeral 101.

Fastener 101 is similar in many respects to fastener 11, the principal differences between the two fasteners being that fastener 101 comprises a head 103 made entirely out of a non-bioabsorbable material and that fastener 101 comprises a flange 105 comprising a core 105-1 and a coating 105-2, core 105-1 being made out of a non-bioabsorbable material and coating 105-2 being made out of a bioabsorbable materials 105-2 having a desired degradation rate. (It should be understood that the non-bioabsorbable material used to make all of fastener 101, except for coating 105-2, could be replaced with a bioabsorbable material having a slower degradation rate than coating 105-2.)

As can readily be appreciated, fastener 101 could be modified by replacing head 103 with head 23 of fastener 11, head 69 of fastener 61, head 89 of fastener 81 or the like. Alternatively, fastener 101 could be modified by replacing flange 105 with a flange made entirely out of the bioabsorbable material of coating 105-2 and/or by replacing head 103 with a head made entirely out of the bioabsorbable material of coating 105-2.

Figure 8:
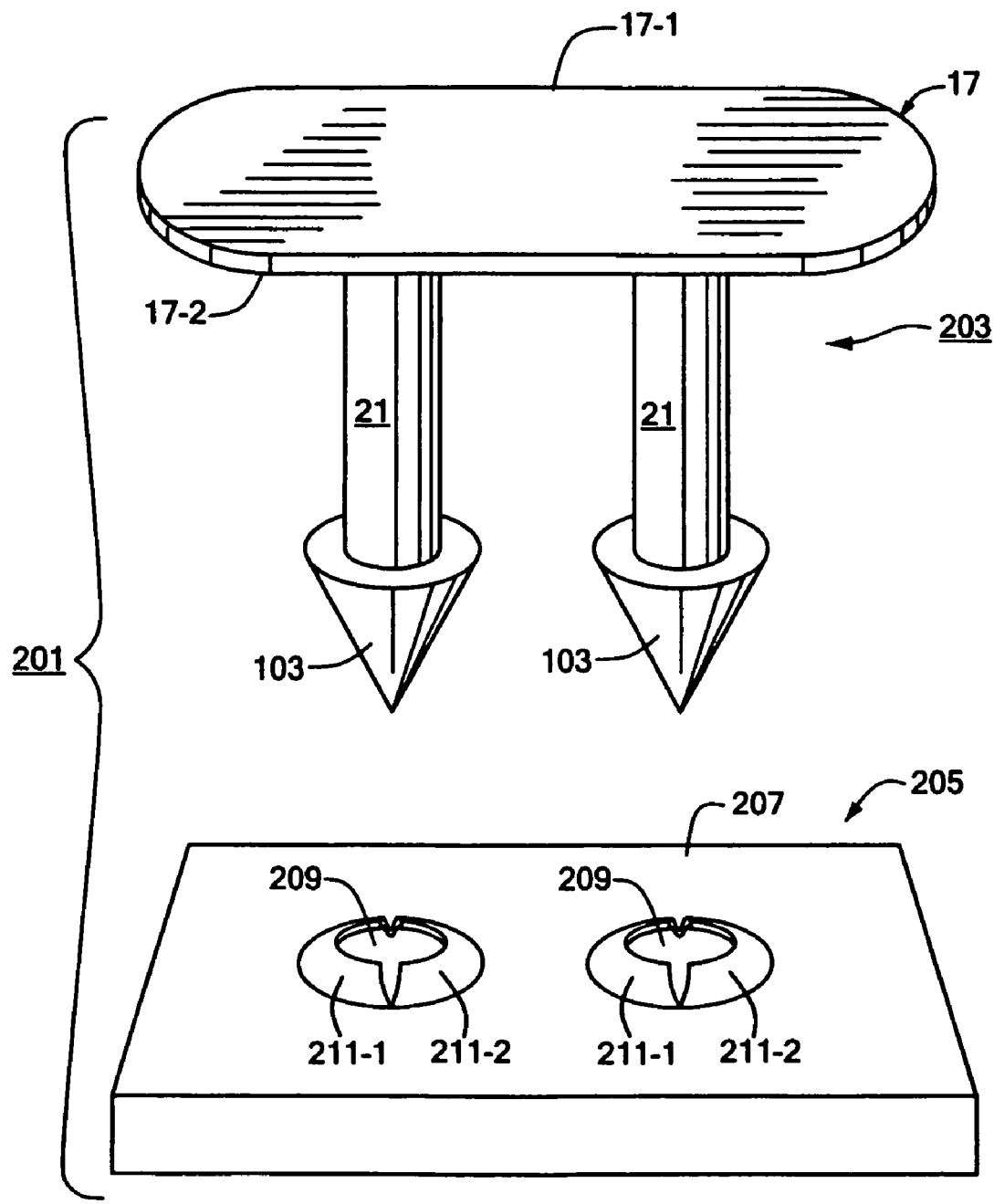
FIG. 8 is a perspective view of a fifth embodiment of a biocompatible fastener constructed according to the teachings of the present invention, the biocompatible fastener being shown in an unassembled state.

Referring now to FIG. 8, there is shown a perspective view of a fifth embodiment of a biocompatible fastener constructed according to the teachings of the present invention, the biocompatible fastener being represented generally by reference numeral 201.

Fastener 201 is similar in many respects to fastener 101, fastener 201 comprising a male portion 203 and a female portion 205. Male portion 203 is identical to the male portion of fastener 101.

Female portion 205 comprises a base 207, which in the present embodiment is generally rectangular in shape. Base 207 is made out of a non-bioabsorbable material and is shaped to include a pair of transverse bores 209, each bore 209 being adapted to receive a head 103. A pair of flanges 211-1 and 211-2 made of a bioabsorbable material are disposed within each bore 209, flanges 211-1 and 211-2 being sized and shaped so that, once head 103 is inserted therepast, head 103 cannot easily be withdrawn from bore 209 back past flanges 211-1 and 211-2, unless flanges 211-1 and 211-2 have degraded sufficiently. Flanges 211-1 and 211-2 are preferably formed by insert-molding. Alternatively, in another embodiment, bore 209 and flanges 211-1 and 211-2 could be separately constructed as an insert that is press-fit into a larger bore (not shown) previously formed in base 207.

As can readily be appreciated, the number of heads 103 and bores 209 in fastener 201 is illustrative only, and it is to be understood that, in other embodiments, there could be as few as one head 103 and one bore 209 or as many as three or more sets of heads 103 and bores 209. Also, it can readily be appreciated that head 103 could be replaced with any of heads 23, 69 or 89.

Figure 9A:
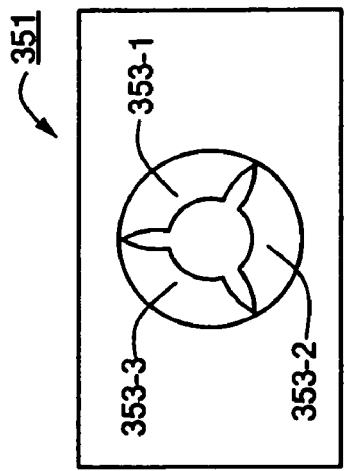
FIGS. 9(a) through 9(d) are top views of alternative embodiments of the female portion of the biocompatible fastener of FIG. 8.

Referring now to FIGS. 9(a) through 9(d), there are shown various alternative embodiments of female portion 205 of fastener 201. In FIG. 9(a), a female portion 301 is shown that is adapted for use with a one-headed male portion, female portion 301 additionally differing from female portion 205 only in that it includes a generally disc-shaped base 303.

Figure 9C:
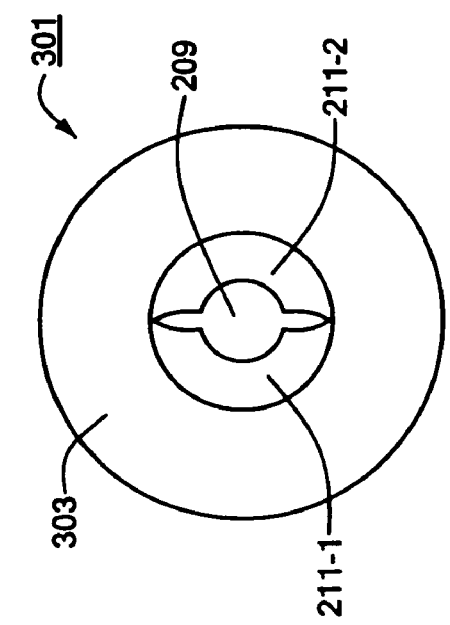
Figure 9B:
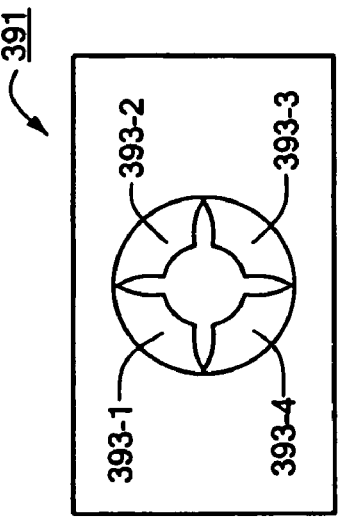

In FIG. 9(b), there is shown another female portion 351 that is adapted for use with a one-headed male portion, female portion 351 additionally differing from female portion 205 only in that it includes three flanges 353-1 through 353-3, instead of two flanges.

In FIG. 9(c), there is shown still another female portion 371 that is adapted for use with a one-headed male portion, female portion 371 differing from female portion 351 only in that it includes five flanges 373-1 through 373-5, instead of three flanges.

Figure 9D:
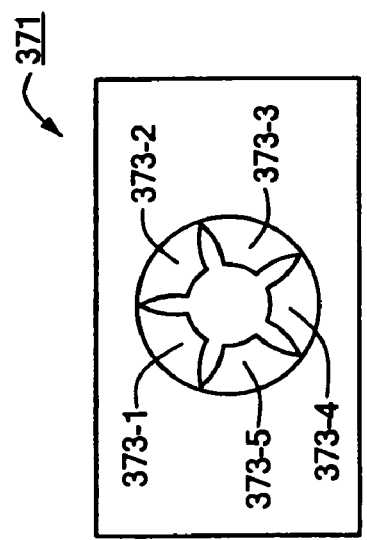

In FIG. 9(d), there is shown still yet another female portion 391 that is adapted for use with a one-headed male portion, female portion 391 differing from female portion 371 only in that it includes four flanges 393-1 through 393-4, instead of five flanges.

It can readily be appreciated that the number of flanges in female portions 205, 301, 351, 371 and 391 are illustrative only and that other numbers of flanges could be substituted. It can also readily be appreciated that female portions 351, 371 and 391 could be modified to include bases having a shape other than rectangular.

The biocompatible fastener of the present invention is not limited to a two-piece, mating-type fastener and could also be, for example, a bone screw, a surgical staple, or the like, wherein an intermediate portion along the length thereof is made out of a bioabsorbable material having a desired degradation rate and wherein the ends thereof are made out of a non-bioabsorbable material or a bioabsorbable material having a slower degradation rate than the bioabsorbable material of the intermediate portion. In this manner, a biocompatible fastener can be designed that fragments within the intermediate portion in a controllable and predictable manner after a desired period of time.

The embodiments of the present invention recited herein are intended to be merely exemplary and those skilled in the art will be able to make numerous variations and modifications to it without departing from the spirit of the present invention. All such variations and modifications are intended to be within the scope of the present invention as defined by the claims appended hereto.

What is claimed is:

1. A method of fastening together two tissue portions, comprising:
    positioning a medical device adjacent a region of tissue having two tissue portions, the medical device comprising: a male member and a female member, wherein one of the male member and the female member includes a first bioabsorbable material overlying one of a non-bioabsorbable material and a second bioabsorbable material, the first bioabsorbable material having a first degradation rate, and the second bioabsorbable material having a second degradation rate slower than the first degradation rate; and
    inserting the male member inside the female member so as to inhibit withdrawal of the male member from the female member and with the two tissue portions between the male member and the female member.

2. The method of claim 1, further comprising permitting the first bioabsorbable material to degrade in the body, wherein degradation of the first bioabsorbable material in the body permits withdrawal of the male member from the female member.

3. The method of claim 2, further comprising withdrawal of the male member from the female member.

4. The method of claim 3, wherein the two tissue portions remain fastened together after withdrawal of the male member from the female member.

5. The method of claim 1, wherein the male member includes a post having a head disposed at a first end of the post, and the female member includes a bore adapted to receive the head and a flange extending into the bore.

6. The method of claim 5, wherein the inserting step includes engaging the head with the flange once the head has been inserted past the flange so as to inhibit withdrawal of the head from the bore.

7. The method of claim 6, wherein at least one of the head and the flange comprises an outer coating over an inner core, the outer coating comprising the first bioabsorbable material, the inner core comprising one of the non-bioabsorbable material and the second bioabsorbable material.

8. The method of claim 7, further comprising permitting the first bioabsorbable material to degrade, wherein degradation of the first bioabsorbable material facilitates withdrawal of the head past the flange.

9. The method of claim 7, wherein the outer coating has a predetermined thickness.

10. A method of securing a gastric fundus to an esophagus, comprising:
    inserting a medical device within a body, the medical device comprising: a male member and a female member, wherein one of the male member and the female member includes a first bioabsorbable material overlying one of a non-bioabsorbable material and a second bioabsorbable material, the first bioabsorbable material having a first degradation rate, and the second bioabsorbable material having a second degradation rate slower than the first degradation rate; and
    inserting the male member inside the female member so as to inhibit withdrawal of the male member from the female member and with tissue of the gastric fundus and tissue of the esophagus between the male member and the female member.

11. The method of claim 10, wherein the male member includes a post having a head disposed at a first end of the post, and the female member includes a sleeve defining a bore adapted to receive the head and having a flange extending into the bore, and wherein the inserting step includes engaging the head with the flange once the head has been inserted past the flange so as to inhibit withdrawal of the head from the bore.

12. The method of claim 11, wherein at least one of the head and the flange comprises an outer coating over an inner core, the outer coating comprising the first bioabsorbable material, the inner core comprising one of the non-bioabsorbable material and the second bioabsorbable material.

13. The method of claim 12, further comprising permitting the first bioabsorbable material to degrade in the body.

14. The method of claim 13, wherein degradation of the first bioabsorbable material facilitates withdrawal of the head past the flange.

15. The method of claim 14, wherein the first degradation rate is predetermined and corresponds to a time sufficient for the tissue of the gastric fundus to fuse to the tissue of the esophagus.

16. A method for fastening tissue, comprising:
    positioning a medical device adjacent tissue in a body, the medical device comprising: a male portion and a female portion, the male portion including a post and a head disposed at a first end of the post, and the female portion including a sleeve defining a bore having a flange extending into the bore, wherein at least one of the flange and the head comprises a first material and a second material, wherein the first material is a first bioabsorbable material and the second material is one of a non-bioabsorbable material and a second bioabsorbable material, the first bioabsorbable material having a first degradation rate, and the second bioabsorbable material having a second degradation rate slower than the first degradation rate; and
    engaging the head with the flange so as to inhibit withdrawal of the head from the bore and to fasten the tissue.

17. The method of claim 16, wherein only one of the head and the flange comprises the first bioabsorbable material, the other of the head and the flange comprises one of the non-bioabsorbable material and the second bioabsorbable material.

18. The method of claim 17, further comprising permitting the first bioabsorbable material to degrade in the body.

19. The method of claim 18, wherein degradation of the first bioabsorbable material in the body permits withdrawal of the head from the bore.

20. The method of claim 19, further comprising withdrawal of the head from the bore, and wherein the tissue remains fastened after withdrawal of the head from the bore.

21. The method of claim 19, wherein the first degradation rate is predetermined and corresponds to a time sufficient to fuse the tissue.

22. A method for fastening gastrointestinal tissue, comprising:
    positioning a medical device adjacent gastrointestinal tissue, the medical device comprising: a male member and a female member, wherein one of the male member and the female member includes a first bioabsorbable material overlying one of a non-bioabsorbable material and a second bioabsorbable material, the first bioabsorbable material having a first degradation rate, and the second bioabsorbable material having a second degradation rate slower than the first degradation rate; and inserting the male member inside the female member so as to inhibit withdrawal of the male member from the female member and with at least two portions of the gastrointestinal tissue between the male member and the female member.

23. The method of claim 22, wherein the male member includes a post having a head disposed at a first end of the post, and the female member includes a sleeve defining a bore adapted to receive the head and having a flange extending into the bore, and wherein the inserting step includes engaging the head with the flange once the head has been inserted past the flange so as to inhibit withdrawal of the head from the bore.

24. The method of claim 23, wherein at least one of the head and the flange comprises an outer coating over an inner core, the outer coating comprising the first bioabsorbable material, the inner core comprising one of the non-bioabsorbable material and the second bioabsorbable material.

25. The method of claim 24, further comprising permitting the first bioabsorbable material to degrade in the body, wherein degradation of the first bioabsorbable material facilitates withdrawal of the head past the flange.

26. The method of claim 25, wherein the first degradation rate is predetermined and corresponds to a time sufficient for the at least two portions of the gastrointestinal tissue to fuse.

* * * * *